US010531973B2

(12) United States Patent
Baghaei Roodsari

(10) Patent No.: US 10,531,973 B2
(45) Date of Patent: Jan. 14, 2020

(54) APPARATUS FOR TREATING AND SUPPORTING EXTREMITIES OR A PORTION OF A BODY

(71) Applicant: Roshanak Baghaei Roodsari, Tehran (IR)

(72) Inventor: Roshanak Baghaei Roodsari, Tehran (IR)

( * ) Notice: Subject to any disclaimer, the term of this patent is extended or adjusted under 35 U.S.C. 154(b) by 504 days.

(21) Appl. No.: 15/491,563

(22) Filed: Apr. 19, 2017

(65) Prior Publication Data

US 2018/0193179 A1 Jul. 12, 2018

Related U.S. Application Data

(60) Provisional application No. 62/444,054, filed on Jan. 9, 2017.

(51) Int. Cl.
*A61F 5/00* (2006.01)
*A61F 5/01* (2006.01)

(52) U.S. Cl.
CPC .......... *A61F 5/0102* (2013.01); *A61F 5/0123* (2013.01); *A61F 2005/0134* (2013.01);
(Continued)

(58) Field of Classification Search
CPC ........ A61F 5/0102; A61F 5/0106; A61F 5/01; A61F 5/0111; A61F 5/0123; A61F 5/0127; A61F 2005/0132; A61F 2005/0134; A61F 2005/0137; A61F 2005/0141; A61F 2005/0144; A61F 2005/0146; A61F 2005/0151; A61F 2/68; A61F 2/82; A61F 2002/075; A61F 2002/30131; A61F 2002/30158; A61F 2002/30164; A61F 2002/30247; A61F 2002/30301; A61F 2002/30331; A61F 2002/30405; A61F 2002/3049; A61F 2002/347; A61F 2002/4624; A61F 2002/4632; A61F 2002/4641; A61F 2002/5006; A61F 2002/503; A61F 2002/5033; A61F 2002/5079; A61F 2002/587; A61F 2002/6657; A61F 2002/6664; A61F 2002/6671; A61F 2002/6827; A61F 2002/701; A61F 2002/74; A61F 2002/7615; A61F 2002/825; A61F 2002/9511; A61F 2002/9517; A61F 2002/9534; A61F 2005/0135; A61F 2005/0155; A61F 2220/0008; A61F 2220/0016; A61F 2220/0033; A61F 2220/0041; A61F 2220/0075; A61F 2220/0091; A61F 2230/005; A61F 2230/0054;
(Continued)

(56) References Cited

U.S. PATENT DOCUMENTS

2004/0002674 A1* 1/2004 Sterling ................ A61F 5/0123
602/26
2009/0030356 A1* 1/2009 Maloney ................ A61F 5/0123
602/16
(Continued)

*Primary Examiner* — Kim M Lewis
(74) *Attorney, Agent, or Firm* — Mannava & Kang, P.C.

(57) ABSTRACT

A support device comprising at least one skeleton structure and at least two coupling articles, wherein each of the two coupling articles are connected to an end section of the skeleton structure, such that the support device includes at least four degrees of freedom.

14 Claims, 6 Drawing Sheets

(52) U.S. Cl.
CPC ............... *A61F 2005/0137* (2013.01); *A61F 2005/0146* (2013.01); *A61F 2005/0151* (2013.01); *A61F 2005/0167* (2013.01)

(58) Field of Classification Search
CPC ...... A61F 2230/0078; A61F 2250/0002; A61F 2250/0007; A61F 2250/0008; A61F 2250/001; A61F 2250/0018; A61F 2250/0039; A61F 2250/006; A61F 2250/0065; A61F 2/07; A61F 2/12; A61F 2/2418; A61F 2/2427; A61F 2/243; A61F 2/2436; A61F 2/2439; A61F 2/34; A61F 2/3662; A61F 2/389; A61F 2/46; A61F 2/586; A61F 2/66; A61F 2/6607; A61F 2/80; A61F 2/844; A61F 2/93; A61F 5/0104; A61F 5/0118; A61F 5/013; A61F 5/028
USPC ......................................... 602/16, 27, 28–29
See application file for complete search history.

(56) References Cited

U.S. PATENT DOCUMENTS

| | | | | |
|---|---|---|---|---|
| 2013/0085433 | A1* | 4/2013 | Grant | A61F 5/013 602/16 |
| 2016/0038327 | A1* | 2/2016 | Mason | A61F 5/0123 602/16 |
| 2016/0113831 | A1* | 4/2016 | Hollander | A61H 1/0244 623/31 |
| 2016/0193067 | A1* | 7/2016 | Petursson | A61F 5/30 602/16 |
| 2017/0298981 | A1* | 10/2017 | Sgeirsson | A61F 5/0123 |

* cited by examiner

APPARATUS FOR TREATING AND SUPPORTING EXTREMITIES OR A PORTION OF A BODY

CROSS-REFERENCE TO RELATED APPLICATION

This application claims the benefit of U.S. Provisional Application No. 62/444,054, filed on Jan. 9, 2017, the content of which is expressly incorporated herein by reference thereto.

FIELD OF THE INVENTION

The present disclosure generally relates to an apparatus for treating and supporting extremities or a portion of a body, and more specifically to an apparatus for treating, supporting, stabilizing, improving mobility, and controlling cartilage matrix degradation of a weight-bearing articular joint.

BACKGROUND OF THE INVENTION

Orthopedic braces have been used to promote proper healing of a joint following an injury to, or surgery on, the joint. Braces are also useful as a method to stabilize joints with arthritis, thereby alleviating pain. However, the existing braces are uncomfortable, do not include a proper number of degrees of freedom, and have limited sizes, shapes and orientations.

SUMMARY OF THE INVENTION

In an aspect the support device includes at least one skeleton structure; and at least two coupling articles, wherein each of the two coupling articles are connected to an arm section of the skeleton structure, such that the support device includes at least a first degree of freedom, a second degree of freedom, a third degree of freedom, and a fourth degree of freedom.

In an aspect, the first degree of freedom is in a form of flexion and extension, the second degree of freedom is in a form of adduction and abduction, the third degree of freedom is in a form of translation, and the fourth degree of freedom is a form of rotation.

In another aspect, the at least one skeleton structure comprises a central base, a first arm, and a second arm.

In a further aspect, each of the first and second arms includes a forearm and an upper arm.

In a further aspect, at least one of the first and second arms comprises a wagon and rail system that provides at least a translation movement between the skeleton structure and at least one of the two coupling articles.

In yet another aspect, each of the forearms is connected to its corresponding upper arm by a screw shaft and provides at least a rotational movement between the forearm and its corresponding upper arm.

In an aspect, at least one of the upper arms is connected to the central base by a two-axis hinge configured to allow at least one of (i) a flexion and extension movements and (ii) an adduction and abduction movements.

In a further aspect, each of the at least two coupling articles includes at least one skeleton connector configured to allow at least one of the coupling articles to have a translation movement.

In an aspect, the support device comprising at least one skeleton structure comprising at least a first arm and a second arm; at least one central base; and at least a two-axis hinge movably connecting each of the first arm and the second arm with the at least one central base.

In an aspect, the two-axis hinge is configured to allow at least a flexion and extension movement and an adduction and abduction movement.

In another aspect, each of the first and second arms includes a forearm and an upper arm.

In a further aspect, each of the forearms is connected to its corresponding upper arm by a screw shaft and configured to provide at least a rotational movement between the forearm and its corresponding upper arm.

In yet another aspect, at least one of the first and second arms comprises a wagon and rail system configured to provide at least a translation movement with respect to a coupling article connected to the wagon and rail system.

In an aspect, the device further comprises at least one coupling article translationally connected to the at least one skeleton structure.

In another aspect, the at least one coupling article comprises a skeleton connector that allows the at least one coupling article to have a translation movement.

In a further aspect, the at least one skeleton structure provides at least four degrees of freedom.

In yet another aspect, a support device comprises a first forearm rotatably connected to a first upper arm, a second forearm rotatably connected to a second upper arm, a first two-axis hinge, movably connecting the first upper arm to a central base, a second two-axis hinge, movably connecting the second upper arm to the central base, and at least one coupling article translationally connected to one of the first forearm and the second forearm.

In an aspect, the at least one coupling article comprises at least one skeleton connector.

In another aspect, the device further comprises a wagon and rail system connected to at least one of the first forearm and the second forearm and allows a translation movement between the at least one of the first forearm and the second forearm and the at least one coupling article.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

The present disclosure in its several aspects and embodiments can be more fully understood from the detailed description and the accompanying drawings, wherein.

Throughout this specification and figures like reference numbers identify like elements.

DETAILED DESCRIPTION OF THE INVENTION

It is to be understood that both the foregoing general description and the following detailed description are exemplary and explanatory only, and are intended to provide an explanation of various embodiments of the present teachings.

In its broad and varied embodiments, disclosed herein apparatus, such as support device 100 for treating and supporting extremities or a portion of a body. In an aspect, the support device 100 can include a design and/or configuration that enables the support device 100 to have at least one degree of freedom, such as two degrees of freedom or more, for example at least three degrees of freedom, or four degrees of freedom or more.

Figure 1:
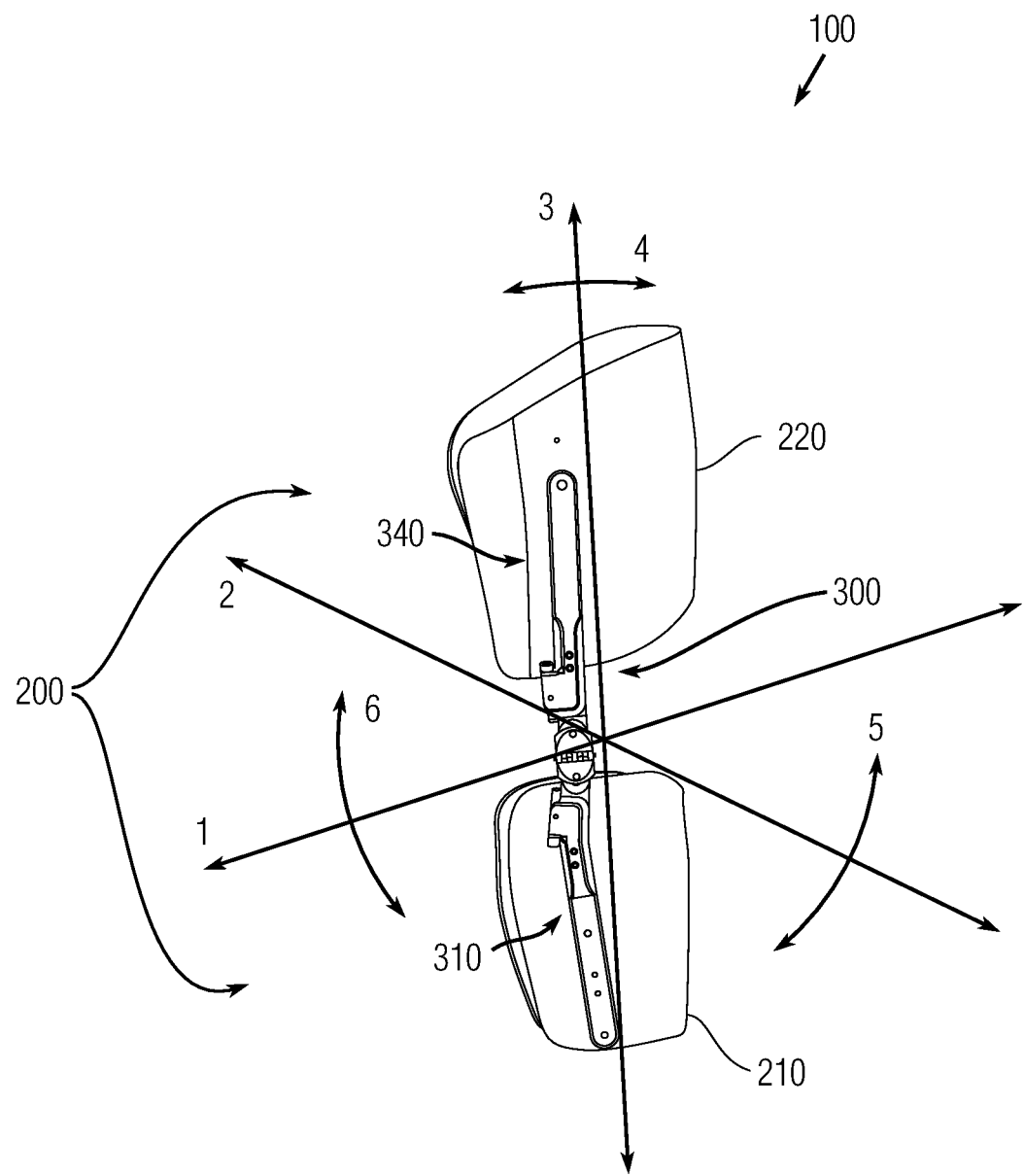
FIG. 1 is a perspective view of the device showing its skeleton and extremity couplers, according to an example of the present disclosure.

In an aspect, when the support device 100 includes at least four degrees of freedom, the first degree of freedom can be in a form of flexion and extension (see rotation 5 in FIG. 1). Furthermore, the second degree of freedom can be in a form of adduction and abduction (see rotation 6 in FIG. 1), the third degree of freedom can be in a form of translation (see movement 3 in FIG. 1), and the fourth degree of freedom can be in a form of rotation (see rotation 4 in FIG. 1).

Figure 2A:
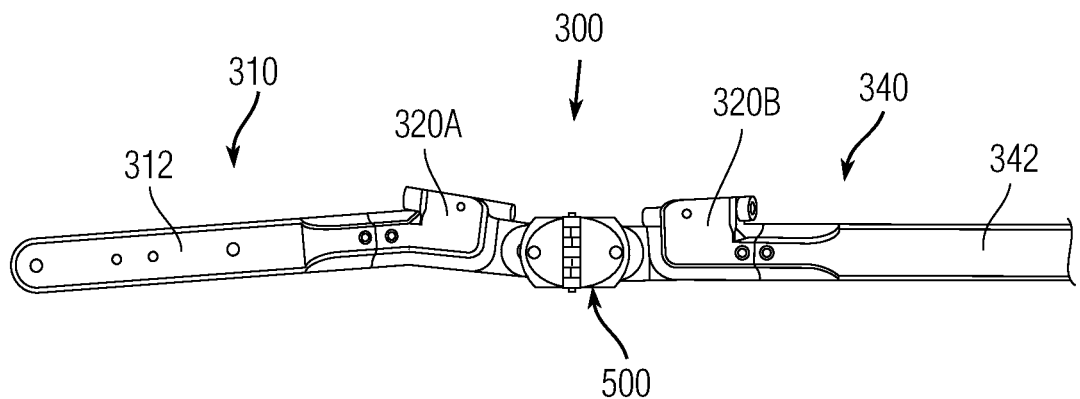
FIG. 2A is a top view of the skeleton portion of the device, according to another example of the present disclosure.
Figure 2B:
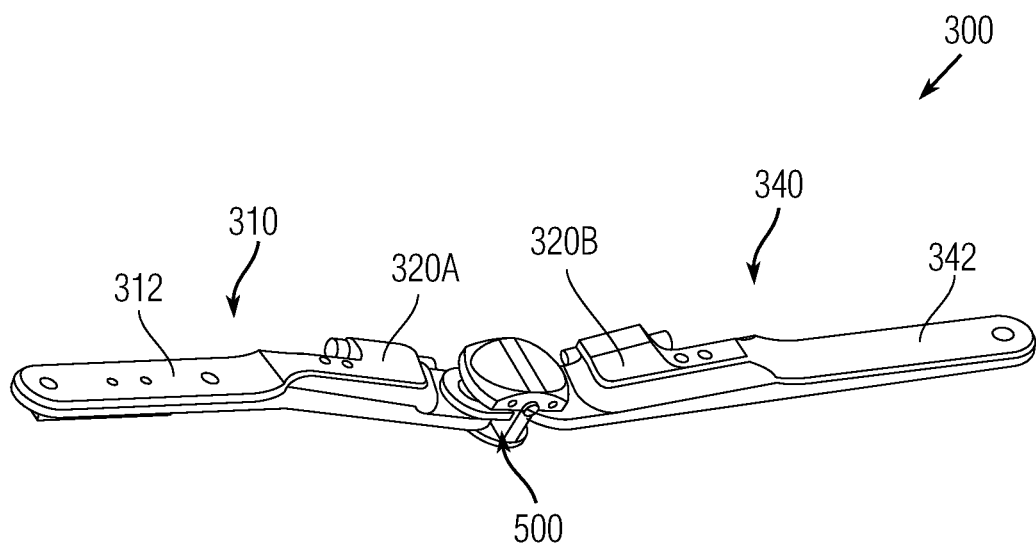
FIG. 2B is a perspective view of the skeleton portion of the device, according to an example of the present disclosure.
Figure 2C:
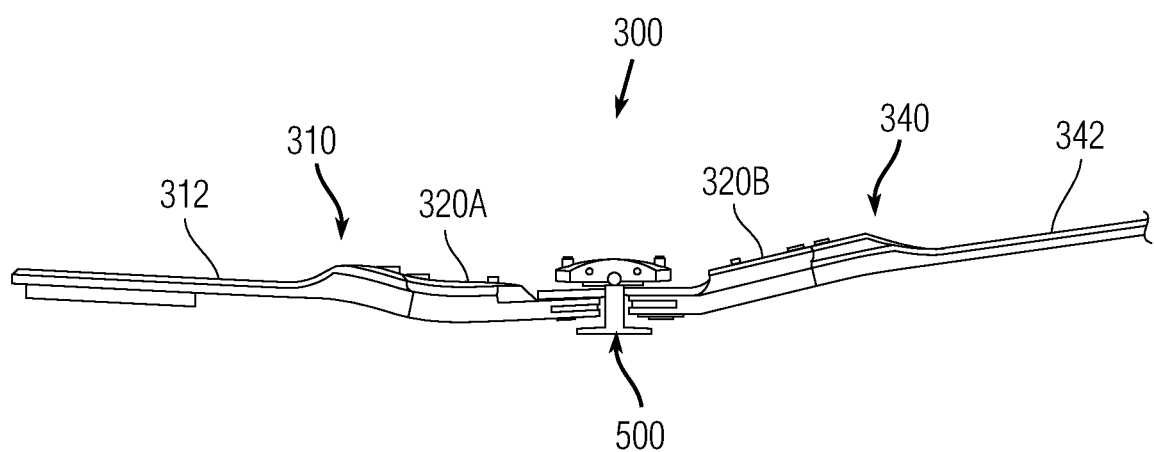
FIG. 2C is a side view of the skeleton portion of the device, according to an example of the present disclosure.

As shown in FIGS. 1-2C, the support device 100 can include a skeleton structure 300 and a coupling articles 200. In one example, the skeleton structure 300 can include first arm 310 and a second arm 340 that can receive and/or be connected to the coupling articles 200. Furthermore, the first arm 310 can include a first forearm 312 and a first upper arm 320A. Similarly, the second arm 340 can include a second forearm 342 and as second upper arm 320B.

In an aspect, the skeleton structure 300 can be made of any material. For example, it can be made of a metallic material, polymeric material, or other natural and manmade materials. For example, the material can be a light-weight material, such as aluminum, polyvinyl chloride (PVC), carbon fiber, fiberglass, para-aramid synthetic fiber, or can be made of heavier materials, such as stainless steel, or can be made of a material such as wood. In an aspect, the material can be a combination of light-weight and heavy materials.

In an aspect, the first forearm 312 and the second forearm 342 can be made of aluminum and can include a length of from about 40 cm or more to about 5 cm or less, for example, each can include a length of from about 35 cm to about 10 cm, such as from about 30 cm, about 25 cm, about 15 cm, or about 20 cm. In an aspect, the length of the first forearm 312 and the second forearm 342 are substantially the same. In another aspect, the length of the first forearm 312 and the second forearm 342 can be different. For example, the first forearm 312 can be shorter or longer than the second forearm 342. When the first forearm 312 includes a length different than the length of the second forearm 342, the length difference can be as little as about 5% or less to about 80% or more. For example, the length difference can be from about 10% to about 70%, such as from about 20% to about 60%, from about 30% to about 50%, or about 40%.

In an aspect, the first upper arm 320A and the second upper arm 320B can include a length of from about 40 cm or more to about 5 cm or less, for example, each can include a length of from about 35 cm to about 10 cm, such as about 30 cm, about 25 cm, about 15 cm, or about 20 cm. In an aspect the length of the first upper arm 320A and the second upper arm 320B are substantially the same. In another aspect, the length of the first upper arm 320A and the second upper arm 320B are different. For example, the first upper arm 320A can be shorter or longer than the second upper arm 320B. When the first upper arm 320A includes a length different than the length of the second upper arm 320B, the length difference can be as little as about 5% or less to about 80% or more. For example, the length difference can be from about 10% to about 70%, such as from about 20% to about 60%, from about 30% to about 50%, or about 40%.

Figure 3:
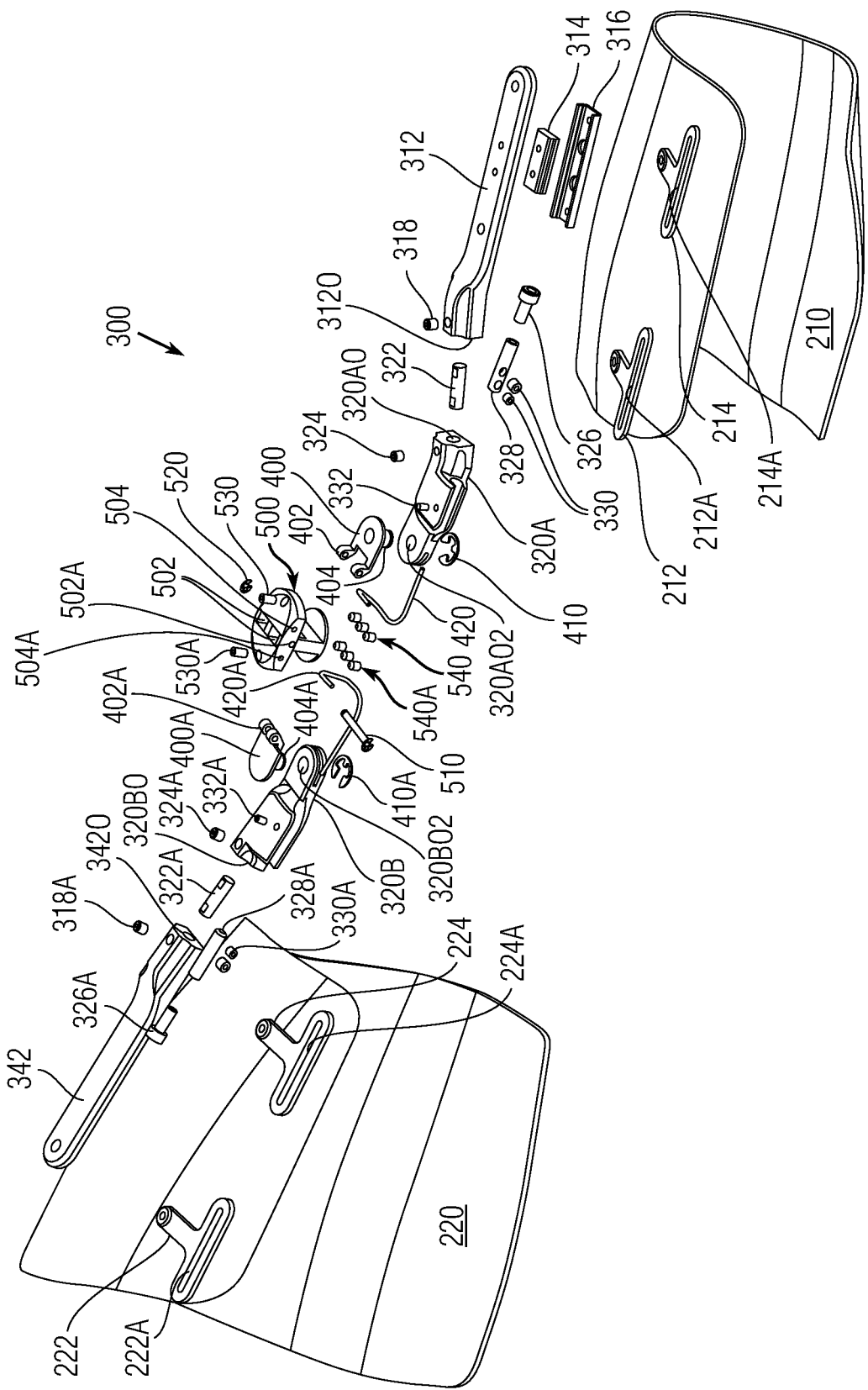
FIG. 3 is a perspective view of each part of the skeleton and the extremity coupler of the device, according to an example of the present disclosure.

In an aspect, the first arm 310 can be connected to the second arm 340 by a central base 500. The central base 500 can be in direct contact with the first arm 310 and the second arm 340. Alternatively, as illustrated in FIG. 3, the central base 500 can be indirectly be connected to the first arm 310 and the second arm 340. For example, the first upper arm 320A can be connected to the central base 500 through a hinge, such as two-axis hinge 400. The two-axis hinge 400 can allow the first arm 310 to have at least one of (i) a flexion and extension movements and/or (ii) an adduction and abduction movements. The design of the two-axis hinge 400 is further described below in more detail. Similarly, the second upper arm 320B can be connected to the central base 500 through a hinge, such as a two-axis hinge 400A. The two-axis hinge 400A can allow the first arm 310 to have at least one of (i) a flexion and extension movements and/or (ii) an adduction and abduction movements. The design of the two-axis hinge 400A can be similar to the two-axis hinge 400 that is further described below in more detail.

Referring to FIGS. 1-2C, the coupling articles 200 can include a first extremity coupler 210 and a second extremity coupler 220. The first extremity coupler 210 and the second extremity coupler 220 can be made of the same or different materials. For example, the first extremity coupler 210 and the second extremity coupler 220 can include an inner layer having a soft polymer based material, such as polyurethane foam, and an outer layer having a hard polymer based material, such as PVC. In another aspect, the first extremity coupler 210 and the second extremity coupler 220 can be made of one or more materials, such as carbon, resins/polymers, textile, metals, or a combination thereof. In an aspect, the first extremity coupler 210 and the second extremity coupler 220 can have a same size and shape. In another aspect, the first extremity coupler 210 can include a size and/or a shape to comfortably be secured to a first part of an extremity, such as a cnemis of a leg or a forearm of an arm and the second extremity coupler 220 can include a size and/or a shape to comfortably secure to a second part of an extremity, such as a thigh of a leg or an upper arm of an arm.

In an aspect, the first extremity coupler 210 and the second extremity coupler 220 can be directly or indirectly connected to a portion of the skeleton structure 300. In an aspect, as shown in FIG. 3, the first extremity coupler 210 can include at least one skeleton connector, such as two skeleton connectors 212 and 214. Similarly, the second extremity coupler 220 can include at least one skeleton connector, such as two skeleton connectors 222 and 224. In an aspect, one or more of the skeleton connectors 212, 214, 222, and 224 can be made of any material, such as metal, polymer, or any other types of material known to one skilled in the art. For example, the skeleton connectors 212, 214, 222, and 224 can be made of aluminum, PVC, graphite, carbon fibers, or a combination thereof. In one example, one or more of the skeleton connectors 212, 214, 222, and 224 can be configured and/or designed such that the skeleton structure 300 can have a translation movement with respect to its corresponding extremity coupler. In an aspect, one or more of the skeleton connectors 212, 214, 222, and 224 can include an orifice or an opening. The shape and size of the opening can vary depending on the mechanism and the device used to connect the one or more of the skeleton connectors 212, 214, 222, and 224 to the skeleton structure 300.

As shown in FIG. 3, each of the skeleton connectors 212, 214, 222, and 224 can be shaped substantially like the letter "T" and can include an elongated opening 212A, 214A, 222A, and 224A, respectively. However, the skeleton connectors 212, 214, 222, and 224 can also include other shapes, such as rectangle, triangle, circle, etc. In one example, the openings can be substantially the length of arms 310 and 340 or less. For example, the length of one or more of the openings 212A, 214A, 222A, and 224A can be from about 80 cm or less, such as about 40 cm or less, such as about 35 cm or less, about 30 cm or less, about 25 cm or less, about 20 cm or less, about 15 cm or less, about 10 cm or less, about 5 cm or less, about 3 cm or less, such as about 2.5 cm.

In an aspect, at least one of the skeleton connectors 212, 214, 222, and 224 can be connected to a portion of the skeleton structure 300, such as the first forearm 312, by an intervening device. As shown in FIG. 3, an example of such an intervening device can be a rail and wagon system having a wagon 314 and a rail 316. In one example, the wagon 314 can be connected to one of the forearms 312 and 342 and the rail 316 can be connected to its corresponding skeleton connector 212, 214, 222, and 224, such that there can be a translational movement between the skeleton structure 300 and at least one of the extremity couplers 210, 220.

In an aspect, as shown in FIG. 3, the wagon 314 and the rail 316 can be associated with and/or are present on a portion of the first arm 310, such as on the first forearm 312 and/or on the first upper arm 320A. In this aspect, the wagon 314 and the rail 316 may not be associated with the second arm 340. In another aspect, not shown in the figures, the wagon 314 and the rail 316 are associated with and/or present on a portion of the first arm 310 and the second arm 340. For example, a first wagon 314 and rail 316 can be connected to at least one of the first forearm 312 and/or the first upper arm 320A and a second wagon 314 and rail 316 (not shown in the Figs.) can be connected to at least one of the second forearm 342 and/or the second upper arm 220B.

In summary, the connection configuration between at least one of the (i) first extremity coupler and first forearm and (ii) the second extremity coupler and the second forearm results in a translation movement.

In an aspect, each of the forearms 312 and 342 can be connected to its respective upper arms 320A and 320B. In one example, the connecting surface of the first forearm 312 can include a first forearm opening or hole 312O and the connecting surface of the first upper arm 320A can include a first upper arm opening or hole 320AO. Similarly, the connecting surface of the second forearm 342 can include a second forearm opening or hole 342O and the connecting surface of the second upper arm 320B can include a second upper arm opening or hole 320BO. In one example each set of openings 312O and 320AO and 342O and 320BO can be configured to face one another, as shown in FIG. 3. To connect the first forearm 312 to the first upper arm 320A, a screw shaft 322 can be inserted in to the openings 312O and 320AO. Similarly, to connect the second forearm 342 to the second upper arm 320B, a screw shaft 322A, can be inserted in to the openings 342O and 320BO.

In an example, each of the shaft screws 322 and 322A has a diameter that is smaller than the diameter of its corresponding openings 312O, 320AO, 342O, and 320BO so that each of the shaft screws 322 and 322A can be inserted into its corresponding openings. Moreover, once each of the shaft screws 322 and 322A has been inserted into its corresponding openings 312O, 320AO and 342O and 320BO, the shaft screws 322 and 322A can be secured by screws 318, 318A, 324, and 324A. In one example, each of the screws 318, 318A, 324, and 324A can be a set screw.

In an aspect, each of the forearms 312 and 342, each of the upper arms 320A and 320B, and each of the screw shafts 322 and 322A are designed and/or configured to allow each of the forearms 312 and 342 to twist or rotate with respect to its corresponding upper arms 320A and 320B. In one example, the diameter of the screw shafts 322 and 322A are sufficiently small enough to allow substantially free rotation between the each of the forearms 312 and 342 and its corresponding upper arms 320A and 320B. In another example, each of the screw shafts 322 and 322A can include a diameter that allows each of the forearms 312 and 342 to friction fittingly connect to its corresponding upper arms 320A and 320B. However, in this exemplary aspect, the screw shafts 322 and 322A can be made of a material that allows the screw shafts 322 and 322A to twist or rotate, thereby, allowing each of the forearms 312 and 342 to twist with respect to its corresponding upper arms 320A and 320B. In this exemplary aspect, the screw shaft material can be hard rubber or any other material that is capable of deforming (e.g., twisting) under a force and returning back to its original status once the force has been removed.

The connection between each of the forearms 312 and 342 and its corresponding upper arms 320A and 320B provides the support device 100 a rotation movement.

In an aspect, each of the arms 310 and 320 can be extended by one or more arm leafs, not shown in the figures, positioned between the forearms 312 and 342 and the upper arms 320A and 320B. Each arm leaf can include an opening or a hole at each end corresponding to each forearm openings 312O and 342O and upper arm openings 320AO and 320BO and can be connected and secured to the each forearm and upper arm by a shaft screw.

As stated above, each of the upper arms 320A and 320B can be connected to the central base 500, such that the support device 100 includes flexion and extension movements in addition to adduction and abduction movements. This can be accomplished by connecting each upper arm 320A and 320B to the central base 500 using two-axis hinges 400 and 400A. The two-axis hinge 400 can include a first hinge portion 402 designed and/or configured to provide an adduction and abduction movement and a second hinge portion 404 designed and/or configured to provide a flexion and extension movement. Similarly, the two-axis hinge 400A can include a first hinge portion 402A designed and/or configured to provide an adduction and abduction movement and a second hinge portion 404A designed and/or configured to provide a flexion and extension movement.

Referring to FIG. 3, first hinge portions 402 and 402A that are designed and/or configured to provide an adduction and abduction movement can include at least one prong, such as two prongs, having an opening. Each prong of the first hinge portions 402 and 402A can be inserted into the central base opening 502 and be rotatably secured to the central base 500 via a rod 510. The rod 510 can be inserted into an opening 502A of the central base 500, pass through the openings in each prong of the first hinge portions 402 and 402A, and be secured by a clip 520. Furthermore, the abduction movement between each arms 310, 340 and the central base 500 can be adjusted and/or controlled by abductions adjustment screws 530 and 530A, each of which can be inserted into the central base 500.

The second hinge portions 404 and 404A can include a design and/or a configuration to provide a flexion and extension movement. Each of the second hinge portions 404 and 404A can include a protrusion that can rotatably lay or rest in its corresponding aperture and/or opening 320AO2 and 320BO2. Each of the second hinge portions 404 and 404A can be rotatably secured to its respective upper arm 320A and 320B via a clip, such as clips 410 and 410A.

Additionally, the first arm 310 and the second arm 340 are connected to the central base 500 by movement transformation wires 420 and 420A. The movement transformation wires 420 and 420A are tension resistant but are not pressure resistant. Thus each of the movement transformation wires 420 and 420A can move unilaterally. Furthermore, each of the movement transformation wires 420 and 420A can be secured to the central base 500. In an aspect, one end of each of the movement transformation wires 420 and 420A can be inserted into a portion of the central base 500 and can be secured to the base by one or more corresponding screws 540 and 540A. For example, the one end of the movement transformation wires 420 and 420A can be inserted in to openings 504 and 504A, respectively and then be secured in the openings 504 and 504A by one or more corresponding screws 540 and 540A. A portion of each of the movement transformation wires 420 and 420A that is away from the end connected to the central base 500, can be inserted into wire cases 328 and 328A, respectively. Each of the movement transformation wires 420 and 420A can then be secured to its respective wire cases 328 and 328A by a set of screws 330 and 330A. In an aspect, each end of the wire cases 328 and 328A can include case adjustment screws 326 and 326A. Each of the case adjustment screws 326 and 326A can be in contact with its corresponding movement transformation wires 420 and 420A so that a user can adjust the final angle of the extension as well as the starting angle of extension and abduction. In an aspect, each of the wire cases 328 and 328A including the movement transformation wires 420 and 420A, and the case adjustment screws 326 and 326A can be connected to a portion of its corresponding upper arms 320A and 320B.

In an aspect, each of the upper arms 320A and 320B can include a slot-like configuration that enables each of the upper arms 320A and 320B to accept its corresponding wire casings 328 and 328A. Furthermore, case securing screws 332 and 332A can secure its corresponding wire cases 328 and 328A in each of the slot-like configurations.

EXPERIMENTS

Experiment 1

Two volunteer subjects, as shown in Table 1, participated in this study.

TABLE 1

Descriptive Characteristics of the Two Subjects

| subject | Gender | Age (years) | Weight (kg) | Height (cm) | BMI (kg/m2) |
|---|---|---|---|---|---|
| 1 | female | 61 | 69 | 154 | 29.01 |
| 2 | female | 56 | 86 | 171 | 29.41 |

Referred subjects were assigned to participate in this study according to the following inclusion and exclusion criteria. Pain in one or both knees, with grade 1 or 2 knee medial compartment osteoarthritis according to the Kellgren/Lawrence (KL) Scale, which ranges from severity 0-4, with zero being the lowest rating considered as inclusion criteria in this study. Subjects who had received any injury, or invasive treatment including injection therapy for the knee during the past 6 months, neurological disease, a symptomatic spine, hip, ankle or foot disease, skin problems, or any disease, which made it difficult to apply a brace (e.g. due to arthritis in the hand or difficulty in bending) were excluded from study. Subjects wore a knee orthoses on the affected side. The ethical committee of University of Social Welfare and Rehabilitation Sciences approved the performance of this study and the subjects signed an informed consent form.

Subjects used the inventive support device (knee unloader orthosis). The knee unloader orthoses were custom molded and individually constructed from a cast of each subject's lower extremity. Valgus correction was performed manually during the casting process by an experienced orthotist. The knee was corrected in the frontal plane to a less-varus position while the patient was sat down with the knee extended. It was corrected to the maximal corrected position which was still comfortable for the patient. All orthoses construction was also performed by an experienced orthotist.

The design of the new knee orthosis was based on the convert knee flexion to abduction to prevent of knee joint varus in gait cycle. In end of the swing, needed varus position provided for positioning of knee joint in normal position in frontal plane in stance phase. Other purpose in new knee joint design was preparing compliance in subjects when knee joint have flexion position. Consequently convert of flexion to abduction must be active one sided. One pivot of translation and two pivot of rotation were considered in design of new knee orthosis to providing normal knee joint pattern when new knee orthosis was used. FIG. 1 shows the new orthosis that was used in this study.

The gait of two patients was assessed in two conditions and in a random order (i.e. with and without the orthosis in situ). The subjects wore identically-styled lightweight, comfortable footwear for each gait analysis session. The shoe was selected to reflect a typical heel height and pitch which could be worn by subjects. The subjects eventually walked along the walk way of the gait laboratory at their comfortable self-selected speed in each test condition in order to collect five data sets. Kinematics and kinetics data were gathered by a Vicon digital motion capture system (Oxford Metrics, UK), using six cameras (Vicon, Infrared model number 460) at a frequency of 100 HZ and two force platforms set apart and positioned to capture a left and right heel strike (Kistler 9286BA, Switzerland). The knee range of motion maximum, externally applied knee adduction angle, walking speed, cadence and step length were analyzed. The two stance—phase variables of interest were peak adduction angle and mean adduction angle. These variables were extracted and averaged from five individual trials for each subject.

Figure 4:
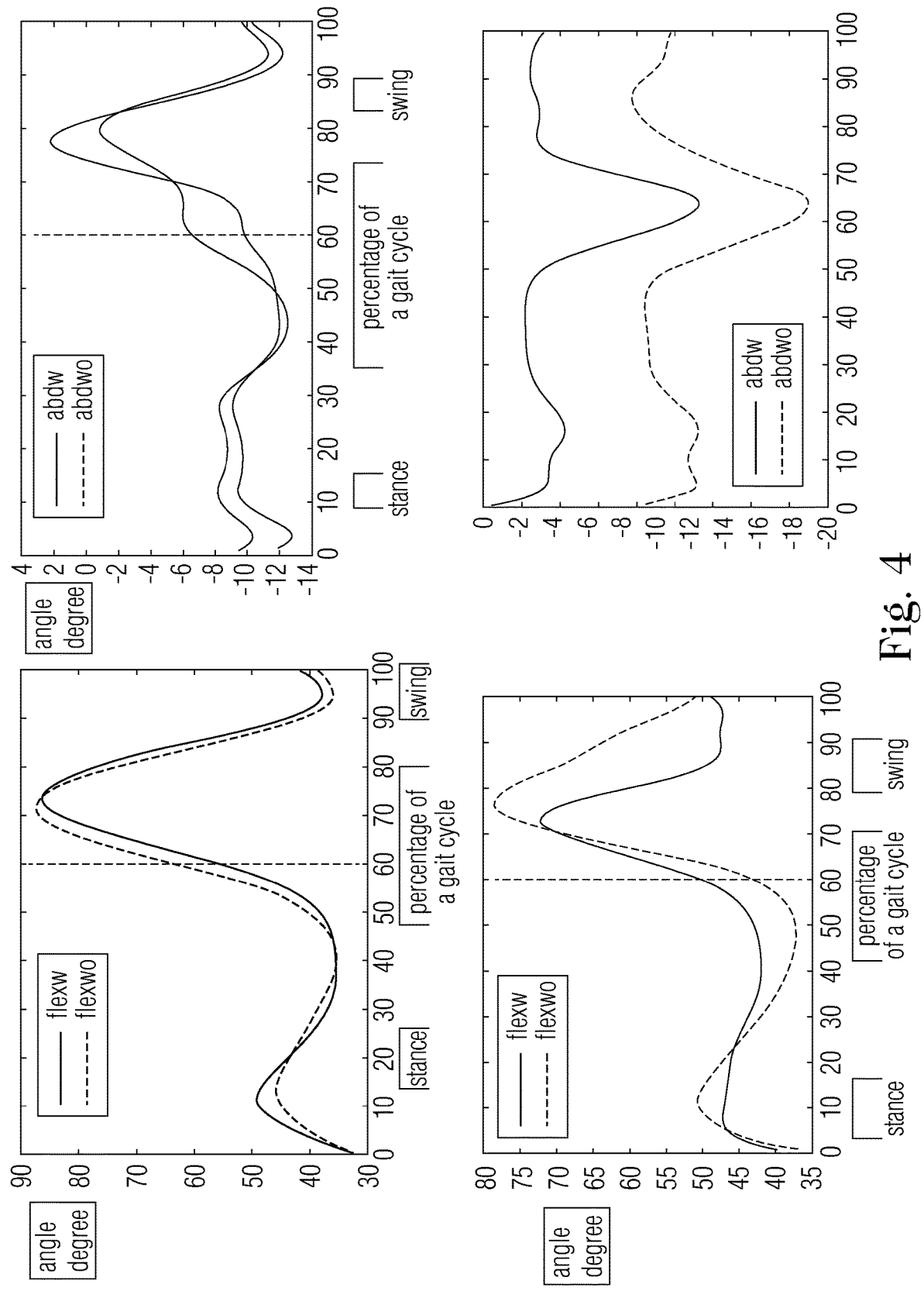
FIG. 4 is a graph showing the overall results of the use of the device.

Tables 2 and 3 show the overall results of use of the new knee orthosis in this study. The external knee adduction angle was significantly reduced (see FIG. 4 and Table 2), and the speed of walking significantly increased when wearing the orthosis. An increase in the knee range of motion, step length was also observed with the orthosis (Tables 2 and 3).

TABLE 2

Flexion/Extension Angle (°) of the Knee and Maximum Knee Adduction Angle in Stance and Swing Phase on the Affected Side with and Without Orthosis

| subject | Knee flexion stance maximum(Degree) | | Knee flexion swing maximum(Degree) | | Maximum knee adduction angle in stance phase(degree) | | Maximum knee adduction angle in swing phase(degree) | |
|---|---|---|---|---|---|---|---|---|
| | with brace | without brace | with brace | without brace | with brace | without brace | with brace | without brace |
| 1 | 24.46 | 25.51 | 46.19 | 44.728 | 2.3 | 4.25 | 11.78 | 11.76 |
| 2 | 44.94 | 46.13 | 56.04 | 54.386 | 2.34 | 5.3 | 1.71 | 1.75 |

TABLE 3

Temporal - Spatial Parameters of Walking on the Affected Side with and Without Orthosis

| subject | Speed (m/s) | | cadence (steps/min) | | Stance phase (% of cycle) | | Stride length (m) | | Stride time (sec) | | Double limb Support time (Sec) | |
|---|---|---|---|---|---|---|---|---|---|---|---|---|
| | with brace | without brace | with brace | without brace | with brace | without brace | with brace | without brace | with brace | without brace | with brace | without brace |
| 1 | 0.93 | 0.88 | 91.24 | 89.60 | 62.68 | 63.53 | 1.145 | 1.125 | 1.24 | 1.32 | 0.16 | 0.164 |
| 2 | 0.748 | 0.684 | 68.965 | 62.50 | 61.05 | 63.37 | 1.45 | 1.142 | 1.66 | 1.815 | 0.21 | 0.434 |

Experiment 2

The participant was tested in five conditions: without brace, resin shell brace with corrective mechanism joint (RWM), resin shell brace without corrective mechanism joint (RWOM), aluminum shell brace with corrective mechanism joint (ALWM), and aluminum shell brace without corrective mechanism joint (ALWOM). Testing session started by the without brace condition (baseline). Between trials with different interventions, subject performed trials without brace (washout trials) to avoid a carry-over effect from the last tested condition. The participant did not receive any information on different adjustments of the orthosis.

Fifteen passive reflective markers (14 mm diameter) were attached to the skin over the right and left selected bony landmarks defining pelvis, thigh, shank, and foot. The three-dimensional coordinate data of the markers were recorded using five Vicon® VCAM motion capture calibrated cameras (Oxford Metrics, Oxford, UK) at the sampling frequency of 100 Hz. Reconstruction and labeling were performed using Vicon® Workstation software (Oxford Metrics, Oxford, UK).

The participant walked barefooted at her self-selected speed. An average of five valid trials per condition was used for analysis. A trial was considered valid if all markers were recognized by the motion capture system. The subject performed some familiarization trials before data collection to achieve a natural gait pattern.

Data Analysis

The kinematic data were first filtered using a Woltring filter with a predicted mean square error of 10 mm. Two groups of variables were extracted for analysis; i.e. standard gait spatiotemporal variables and peak knee joint angles. The standard spatiotemporal variables were walking speed, stride length and stride time of affected limb, cadence and stance phase, and double support phase of affected limb.

Walking speed was calculated as the distance covered by the sacrum marker divided by time. Stride length and time were calculated as the distance and time between two consecutive heel strikes of the same foot, respectively. Heel strikes were identified as the minima of the heel marker time series in vertical direction. Cadence was determined as step/min. In addition, to calculate peak knee joint angles first, knee flexion/extension and adduction/abduction angles were extracted using Vicon® Workstation software (Oxford Metrics, Oxford, UK). Consequently, peak knee flexion/extension and adduction/abduction angles in both stance and swing phases were identified.

Findings and Outcomes

The results of spatiotemporal variables of gait under different brace conditions as well as their percent of changes relative to the without brace condition is presented in Table 4. According to the results, the RWM condition had the maximum effect on the participant's walking speed (43.52%). RWM brace also had the highest effect on the cadence of the OA participant compared to the other conditions. In addition, results demonstrated that in comparison to the without brace condition, the RWM brace reduced the stance phase of the gait cycle more than other brace conditions (10.38%). Furthermore, both stride length and stride time increased by 17.5% and 13.63%, respectively, mostly under the RWM condition. Finally, RWM condition had the greatest effect on the reduction of double support phase with 33% of reduction.

Figure 5:
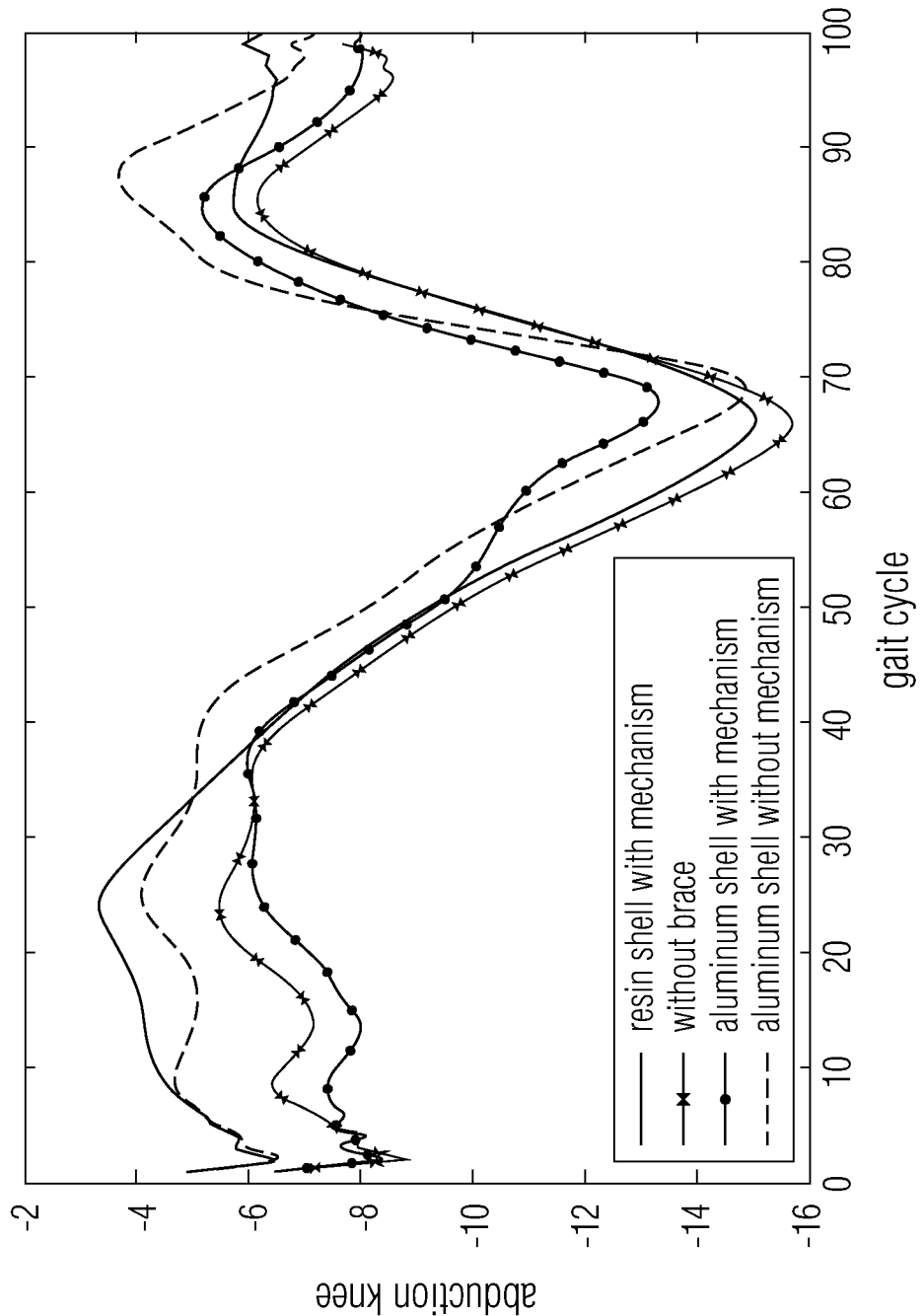
FIG. 5 is a graph showing abduction versus the gait cycle.

The results of different brace conditions on the maximum knee flexion and abduction angles are presented in Table 5 and FIG. 5. In stance phase, the RWM brace had the highest reduction in maximum knee flexion (5.81%) compared to without brace condition. In swing phase; however, ALWM resulted in higher decrease of maximum knee flexion (4.46%). In addition, for maximum knee abduction angle, RWOM had the highest reduction (37.55%) in stance while ALWM provided the highest reduction in swing phase (33.12%). In addition, according to FIG. 5, the RWM brace produced the highest abduction angle during the stance phase.

TABLE 4

Gait Spatiotemporal Variables in Five Test Conditions

| | Speed (m/s) | Percent Increase | Cadence (step/min) | Percent Increase | Stance phase of affected limb (%) | Percent decrease | Stride length Of affected limb (m) | Percent Increase | Stride time of affected limb (s) | Percent Increase | Double support time (s) | Percent decrease |
|---|---|---|---|---|---|---|---|---|---|---|---|---|
| Without brace | 0.55 | | 56.60 | | 68.18 | | 0.937 | | 1.76 | | 0.21 | |
| RWM[1] | 0.79 | 43.52% | 60.60 | 7.06% | 61.10 | 10.38% | 1.10 | 17.5%0 | 2.00 | 13.63% | 0.14 | 33.00% |
| RWOM[2] | 0.57 | 2.51% | 58.25 | 2.91% | 62.70 | 8.03% | 0.96 | 2.45% | 1.81 | 2.84% | 0.17 | 19.05% |
| ALWM[3] | 0.63 | 13.30% | 57.69 | 1.92% | 66.30 | 2.75% | 1.02 | 8.96% | 1.84 | 4.54% | 0.14 | 33.00% |
| ALWOM[4] | 0.56 | 0.71% | 55.40 | −2.12% | 67.06 | 1.64% | 0.97 | 3.84% | 1.77 | 0.56% | 0.18 | 14.28% |

[1]Resin shell brace with corrective mechanism joint
[2]Resin shell brace without corrective mechanism joint
[3]Aluminum shell brace with corrective mechanism joint
[4]Aluminum shell brace without corrective mechanism joint

TABLE 5

Maximum Value of Knee Flexion and Abduction in Stance and Swing Phases of the Gait Cycle in different Brace Conditions, Percentages of Relative Decrease of Flexion and Abduction Angles in Stance and Swing Phase

| | Maximum knee flexion (degrees) | | | Maximum knee abduction (degrees) | |
|---|---|---|---|---|---|
| | Stance | Swing | | Stance | Swing |
| Without brace | 51.41 | 72.57 | Without brace | 6.47 | 6.4 |
| RWM[1] | 48.55 | 73.38 | RWM | 5.36 | 6.00 |
| RWOM[2] | 51.37 | 72.87 | RWOM | 4.04 | 6.01 |
| ALWM[3] | 48.57 | 69.99 | ALWM | 4.92 | 4.28 |
| ALWOM[4] | 48.42 | 69.33 | ALWOM | 4.54 | 4.54 |
| Percentage of decrease relative to without brace condition | | | | | |
| RWM | 5.56% | −1.11% | RWM | 17.15% | 0.61% |
| RWOM | 0.73% | −0.41% | RWOM | 37.55% | 0.60% |
| ALWM | 5.24% | 3.55% | ALWM | 23.95% | 33.12% |

[1]Resin shell brace with corrective mechanism joint
[2]Resin shell brace without corrective mechanism joint
[3]Aluminum shell brace with corrective mechanism joint
[4]Aluminum shell brace without corrective mechanism joint From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

This scope disclosure is to be broadly construed. It is intended that this disclosure disclose equivalents, means, systems and methods to achieve the devices, activities and mechanical actions disclosed herein. For each device, article, method, mean, mechanical element or mechanism disclosed, it is intended that this disclosure also encompass in its disclosure and teaches equivalents, means, systems and methods for practicing the many aspects, mechanisms and devices disclosed herein. Additionally, this disclosure regards a coating and its many aspects, features and elements. Such a device can be dynamic in its use and operation, this disclosure is intended to encompass the equivalents, means, systems and methods of the use of the device and/or article of manufacture and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

I claim:

1. A support device comprising:
    at least one skeleton structure comprising a central base, a first arm, and a second arm wherein each of the first and second arms includes a forearm and an upper arm, and wherein each of the forearms is connected to its corresponding upper arm by a screw shaft and provides at least rotational movement between the forearm and its corresponding upper arm; and
    at least two coupling articles;
    wherein each of the two coupling articles are connected to an arm section of the skeleton structure, such that the support device includes at least a first degree of freedom, a second degree of freedom, a third degree of freedom, and a fourth degree of freedom.

2. The support device of claim 1, wherein the first degree of freedom is in a form of flexion and extension, the second degree of freedom is in a form of adduction and abduction, the third degree of freedom is in a form of translation, and the fourth degree of freedom is in a form of rotation.

3. The support device of claim 1, wherein at least of the first and second arms comprises a wagon and rail system that provides at least a translation movement between the skeleton structure and at least one of the two coupling articles.

4. The support device of claim 1, wherein at least one of the upper arms is connected to the central base by a two-axis hinge configured to allow at least one of (i) a flexion and extension movements and (ii) an adduction and abduction movements.

5. The support device of claim 1, wherein each of the at least two coupling articles includes at least one skeleton connector configured to allow at least one of the coupling articles to have a translation movement.

6. A support device comprising:
    at least one skeleton structure comprising:
        at least a first arm and a second arm, wherein each of the first and second arms includes a forearm and an upper arm and wherein each of the forearms is connected to its corresponding upper arm by a screw shat and configured to provide at least a rotational movement between the forearm and corresponding upper arm;
        at least one central base; and
        at least a two-axis hinge movably connecting each of the first arm and the second arm with the at least one central base.

7. The support device of claim 6, wherein the two-axis hinge is configured to allow at least a flexion and extension movement and an adduction and abduction movement.

8. The support device of claim 6, wherein at least one of the first and second arms comprises a wagon and rail system configured to provide at least a translation movement with respect to a coupling article connected to the wagon and rail system.

9. The support device of claim 6, further comprises at least one coupling article translationally connected to the at least one skeleton structure.

10. The support device of claim 9, wherein the at least one coupling article comprises a skeleton connector that allows the at least one coupling article to have a translation movement.

11. The support device of claim 6, wherein the at least one skeleton structure provides at least four degrees of freedom.

12. A support device comprising:
a first forearm rotatably connected to a first upper arm;
a second forearm rotatably connected to a second upper arm;
a first two-axis hinge, movably connecting the first upper arm to a central base;
a second two-axis hinge, movably connecting the second upper arm to the central base; and
at least one coupling article translationally connected to one of the first forearm and the second forearm.

13. The support device of claim 12, wherein the at least one coupling article comprises at least one skeleton connector.

14. The support device of claim 12, further comprises a wagon and rail system connected to at least one of the first forearm and the second forearm and allows a translation movement between the at least one of the first forearm and the second forearm and the at least one coupling article.

* * * * *